[19] United States Patent
Heitzmann et al.

[11] Patent Number: 6,165,746
[45] Date of Patent: *Dec. 26, 2000

[54] PREVENTING ENDOGENOUS AMINOPEPTIDASE MEDIATED N-TERMINAL AMINO ACID CLEAVAGE DURING EXPRESSION OF FOREIGN GENES IN BACTERIA

[75] Inventors: Markus Heitzmann, Lörrach, Germany; Rao Movva, Basel; Paul Ramage, Reinach, both of Switzerland

[73] Assignee: Novartis AG, Basel, Switzerland

[ * ] Notice: This patent is subject to a terminal disclaimer.

[21] Appl. No.: 08/446,667

[22] PCT Filed: Nov. 29, 1993

[86] PCT No.: PCT/EP93/03349

§ 371 Date: May 26, 1995

§ 102(e) Date: May 26, 1995

[87] PCT Pub. No.: WO94/12659

PCT Pub. Date: Jun. 9, 1994

[30] Foreign Application Priority Data

Nov. 30, 1992 [GB] United Kingdom ................... 9225021

[51] Int. Cl.$^7$ ........................................ C12P 21/06
[52] U.S. Cl. ................. 435/69.1; 435/69.5; 435/69.7; 530/300; 530/350
[58] Field of Search ............... 435/69.1, 69.5, 435/69.8, 240.2, 69.7, 69.2, 64.1, 69.6, 252.3, 252.33, 219

[56] References Cited

FOREIGN PATENT DOCUMENTS

| 204527 | 10/1986 | European Pat. Off. . |
| 219237 | 4/1987 | European Pat. Off. . |
| WO 86/01229 | 2/1986 | WIPO . |

OTHER PUBLICATIONS

Rall, et al., J. Biol. Chem., 257, Table VII, 1982.
Biological Abstracts, vol. 93, No. 3, Feb. 1, 1992, abstract No. 27458.

*Primary Examiner*—Nashaat T. Nashed
*Attorney, Agent, or Firm*—Gabriel Lopez; Diane E. Furman

[57] ABSTRACT

A process for the recombinant preparation in a bacterial host of the mature form of a mammalian protein or peptide of formula X-Pro-Z, which is subject to processing by endogenous bacterial aminopeptidases is provided. In the formula X-Pro-Z, X is a single N-terminal amino acid other than proline, and Z is the remaining sequence of amino acid residues of the protein or peptide. The process comprises inserting into a cell of the bacterial host an appropriate vector containing DNA coding for Met-Y-X-Pro-Z, in which Y is a natural amino acid that is specifically cleavable in vitro from X-Pro-Z by an aminopeptidases and that imparts resistance to in vivo processing by endogenous bacterial aminopeptidases. The cell is then induced to express the expression product Met-Y-X-Pro-Z which is then treated with an appropriate aminopeptidase to cleave off Met and Y.

13 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:1:

Met Xaa Xaa Pro Xaa
1               5

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:2:

Xaa Xaa Pro Xaa
1

(2) INFORMATION FOR SEQ ID NO:3:

(i) SEQUENCE CHARACTERISTICS:
      (A) LENGTH: 5 amino acids
      (B) TYPE: amino acid
      (D) TOPOLOGY: linear (ii) MOLECULE TYPE: peptide -continued

```
        (v) FRAGMENT TYPE: N-terminal (xi) SEQUENCE DESCRIPTION: SEQ ID NO:3:

Met Xaa Ala Pro Xaa
1               5

(2) INFORMATION FOR SEQ ID NO:4:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:4:

Met Xaa Ser Pro Xaa
1               5

(2) INFORMATION FOR SEQ ID NO:5:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:5:

Xaa Ala Pro Xaa
1

(2) INFORMATION FOR SEQ ID NO:6:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:6:

Pro Val Pro Xaa
1

(2) INFORMATION FOR SEQ ID NO:7:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:7:

Met Ala Pro Xaa
```

PREVENTING ENDOGENOUS AMINOPEPTIDASE MEDIATED N-TERMINAL AMINO ACID CLEAVAGE DURING EXPRESSION OF FOREIGN GENES IN BACTERIA

This invention relates to the recombinant production of mammalian proteins and peptides in prokaryotic host cells.

When a protein of mammalian origin is expressed in a bacterial host, for example E. coli, it is normally expressed as a precursor protein which carries a methionine residue (Met) at its N-terminus. This Met residue must be removed to obtain the protein in its natural, mature form. This can be done by use of certain aminopeptidase enzymes, for example aminopeptidase-1 (AP-1) which is obtained from Aeromonas, which are capable of sequentially cleaving N-terminal amino acids from proteins. This cleavage process is halted by certain amino acids or combinations of amino acids which act as "stop signals".

Stop signals for AP-1 include aspartic acid (Asp), glutamic acid (Glu), and the combination X-Pro where X is any amino acid other than proline. Consequently, as described in International Patent publication WO86/01229, this enzyme may be used to cleave specifically the N-terminal Met from a protein, expressed in a bacterial host, that has the N-terminal sequence:

Met-Asp-;
−1  1
Met-Glu-; or
−1  1
Met-X-Pro-.
−1  1  2

However bacterial hosts such as E. coli contain endogenous peptidase enzymes which can cleave the N-terminal residues of certain proteins produced by the bacterium in a non-specific manner. This gives rise to a mixture of products which is often very undesirable. For example, when a protein having Pro in the 2-position is expressed in E. coli, the nascent Met-X-Pro- protein is processed by the N-terminal methionine amino peptidase (MAP) enzyme of E. coli. This enzyme does not recognize X-Pro as a stop signal and not only the Met residue but also the X may be removed.

One example of such a protein is IL-6. IL-6 is a secretory lymphokine which in mammalian cells is generated by the synthesis and processing of a precursor protein having a signal sequence, at the N-terminus, of 28 amino acids. Removal of this signal sequence gives the mature protein of 185 amino acids that has the N-terminal sequence Ala-Pro-Val-. When the recombinant protein is produced in E. coli, a protein coding sequence is used which does not contain codons coding for the signal peptide, but has a start codon preceding the codons coding for the mature protein. On expression, this start codon generates a Met residue so that the initial translational product has the N-terminal sequence:

Met-Ala-Pro. - - - (remainder of IL-6)
−1 +1 2 . . . 185

However partial processing of this product in vivo by the MAP enzyme of E. coli results in a heterogeneous mixture of IL-6 species with different N-termini, as shown below for certain fermentation conditions:

Met-Ala-Pro- - - - 33%
Ala-Pro-. - - - 16%
Pro- - - - 51%

Thus only 16% of the protein product obtained is the desired, mature protein. Further, treatment of this mixture with AP-1 to cleave the Met from the first of these products causes further cleavage of the third product to Val$^3$-Pro$^4$- - - IL-6, which further increases the heterogeneity.

Another example of such a protein is LIF (Leukaemia Inhibitory Factor) which is described in EP 0 285 448. When this protein is produced in E. coli, the initial translational product has the N-terminal sequence:

Met-Ser-Pro- - - - (remainder of LIF)
−1 +1 +2 180

Partial processing of this product by the MAP enzyme of E. coli results in the following heterogeneous mixture of LIF species for certain fermentation conditions:

Met-Ser-Pro- - - - 79%
Ser-Pro- - - - 12%

Hence only 12% of the proteins obtained are the desired, mature protein. Again treatment of the mixture with AP-1 to cleave the Met from the first of these products would cause further cleavage of the third product.

Similar problems occur in the recombinant production in bacterial hosts of many other useful proteins.

Thus it is an object of this invention to provide a process for the production of proteins and peptides in prokaryotic host cells in which processing of the product by endogenous MAP enzymes is reduced.

German patent publication DE 40 39 415 discloses a method of specifically cleaving the N-terminal Met from proteins by causing the bacterial host to express additional amino acids at the N-terminus. An IgA-protease is then used to cleave the Met-Y to leave the protein X-Pro-A. However this German patent publication deals with the problem of obtaining specific cleavage of Met using IgA-protease and does not address the problem of in vivo cleavage of the nascent protein by MAP.

In WO86/01229 it is mentioned that Aeromonas aminopeptidase may be used to cleave Met-Leu-bGH, as well as Met-bGH, to mature bovine growth hormone (bGH). However, there is no suggestion that there is any advantage to be gained by the insertion of Leu, and the problem of in vivo processing by bacterial endogenous aminopeptidases is not mentioned or contemplated.

It has now been found that if the initially translated protein or polypeptide carries a single suitable, additional, amino acid between the N-terminal Met and the first amino acid residue of the mature form of the protein or polypeptide, then the protein or polypeptide is not processed, or is processed only to a small extent, by endogenous MAP. Also the protein or polypeptide is capable of being cleaved specifically to the desired mature form of the protein or polypeptide by an appropriate aminopeptidase.

Accordingly, the present invention provides a process for the recombinant production in a bacterial host of the mature form of a mammalian protein or polypeptide which is subject to processing by endogenous bacterial aminopeptidases, the protein or polypeptide being of formula X-Pro-Z in which X is a single N-terminal amino acid other than proline, and Z is the remaining sequence of amino acid residues of the protein or polypeptide; the process comprising the steps of:

a) transforming bacterial host cells with an appropriate vector containing DNA coding for Met-Y-X-Pro-Z (SEQ. ID NO. 1), in which X and Z are as defined above and Y is a natural amino acid that is specifically cleavable in vitro from Y-X-Pro-Z (SEQ. ID NO. 2) by an aminopeptidase and that imparts resistance to in vivo processing by endogenous bacterial aminopeptidases, into a cell of the bacterial host;

b) inducing the transformed cells to express the product Met-Y-X-Pro-Z;

c) treating the product Met-Y-X-Pro-Z; with an appropriate aminopeptidase to cleave off Met and Y; and d) isolating the protein or polypeptide X-Pro-Z; provided that Y is not Leu when X-Pro-Z is mature bovine growth hormone.

The inclusion of the appropriately selected amino acid residue Y in the Met-Y-X-Pro-Z product provides a large improvement in the homogeneity of the expression products of the bacterial host cells. This in turn results in a large improvement in the homogeneity of the product after treatment with an appropriate aminopeptidase.

Preferably the bacterial host is *E. coli*. The mammalian protein or peptide may be any protein or peptide that has X-Pro as the first two amino acid residues at the N-terminus. Preferred mammalian proteins include IL-6 and LIF. A further example is IL-3 which has the N-terminal sequence Ala$^1$-Pro$^2$-Met$^3$-. The aminopeptidase is preferably obtained from *Bacillus stearothermophilus, Streptomyces griseus* or *Aeromonas*, more preferably from *Aeromonas*. Most preferably it is the aminopeptidase AP-1 from *Aeromonas*, the preparation of which is described by Prescott et al, *J. Biol. Chem.* 246, 1756, (1971).

The Met-Y-X-Pro-Z expression product of step b), is preferably isolated before being treated with an appropriate aminopeptidase. In step d) the desired protein or polypeptide X-Pro-Z is isolated in mature form substantially free from other forms such as Met-Y-X-Pro-Z, Y-X-Pro-Z and Pro-Z.

The choice of the amino acid Y will depend upon the specific mammalian protein or peptide and expression system used, and will be governed by the following properties of the initial expression product Met-Y-X-Pro-Z:

i) The product must be capable of a high level of expression in the host/vector system used;

ii) The product must be resistant to in vivo processing by endogenous bacterial aminopeptidases or must be resistant to any endogenous processing that removes more than Met$^{-1}$; and iii) The product must be specifically cleaved to X-Pro-Z by the aminopeptidase used in step c) above.

Preferably Y will be selected from those amino acids which have long side chains and in particular is selected from Ser, Asn, Gln, His, Arg, Lys, Tyr, Phe, Met, Val, Ile and Leu. The selection of the appropriate amino acid Y can be made on the basis of the known properties of amino acids and appropriate optimization. For example, in certain proteins, selection of Y from Phe, Ile, Leu, Met, Val and His results in specific and fast cleavage of Y from the protein by AP-1. Therefore Y is quite likely to be selected from one of these amino acids if AP-1 is used. However this needs to be balanced against the ability of the amino acid Y to inhibit endogenous MAP cleavage. In certain proteins, Gln, His, Arg, Lys, Tyr, Phe and Met strongly inhibit endogenous MAP cleavage and Asn, Ile and Leu also inhibit cleavage in these proteins. Selection of an amino acid which falls within both groups is therefore quite likely to provide specific AP-1 cleavage and inhibition of endogenous MAP cleavage. The resultant vector should then be tested for adequate expression of the protein.

In tests carried out on the IL-6 system (Met-Y-Ala-Pro-Z (SEQ. ID NO. 3), it is found that no in vivo processing of the protein by MAP occurs when Y is Gln, His, Arg, Lys, Tyr, Phe or Met. When Y is Leu, Ile, or Asn the level of processing is very low; that is only very small amounts of Y-Ala-Pro-Z (SEQ. ID NO. 4) could be detected. However high specificity in cleavage of Met-Y-Ala-Pro-Z by AP-1 to Ala-Pro-Z is obtained when Y is Ile, Leu, His, Phe or Met. Therefore Met-Y-Ala-Pro-Z proteins in which Y is Ile, Leu, His, Phe or Met are appropriate precursors for IL-6. Adequate levels of expression are obtained when Y is His, Phe and Met. Preferably, for IL-6, Y is Phe.

In the LIF system (Met-Y-Ser-Pro-Z (SEQ. ID NO. 5)), when Y is His, Phe and Ile, Met cleavage in vivo is significantly reduced. High specificity in cleavage of Met-Y-Ser-Pro-Z to the mature form by AP-1 is when Y is Phe or Ile. Levels of expression are adequately high for both of these residues. Preferably, for the LIF system, Y is Ile.

The vector containing DNA coding for Y-X-Pro-Z can be prepared by any one of many conventional techniques. Preferably the polymerase chain reaction (PCR) technique is used, to prepare the protein codines sequence using suitable 5' and 3' primers and the DNA coding for the mature protein as template. The DNA can then be cloned into an appropriate vector and the resultant expression vector transfected into a suitable host such as *E. coli*.

Fermentation of the host is then carried out and the host caused to express the required protein. Once a sufficiently high cell density is reached, the cells can be harvested and lysed to release the proteins. This can be done by using osmotic or mechanical techniques. The use of a Manton-Gaulin press usually results in complete disruption. If necessary, the cells may be first treated with a lysozyme to make the cells more vulnerable to disruption. Usually the expressed protein will be in the form of dense inclusion bodies which are collected by centrifugation.

The protein is then solubilized from the inclusion body fraction by treatment with a chaotrope such as guanidine hydrochloride or urea. The resultant solubilized and unfolded protein is then renatured by a suitable technique such as dilution, oxidative refolding, addition of detergent and the like. These techniques are known and examples can be found in EP-A 0 219 874, EP-A 0 114 506 and WO 84/03711.

The refolded protein is then isolated using chromatography techniques suitable for the particular protein. Again these techniques are known.

An aminopeptidase, preferably AP-1, is then added to the isolated protein, usually in a ratio of enzyme:substrate in the range of 1:100 to 1:10000 and more preferably in the range of 1:1000 to 1:5000. Suitable temperatures and reaction times can be selected and the reaction stopped, usually by addition of acid or chromatographic removal of the enzyme, once the required time has been reached. The protein is then further purified using suitable chromatography techniques. If necessary, further purification to remove oxidized forms of the protein and endotoxins can be carried out.

Provided that the aminopeptidase is allowed to act for a sufficient time, greater than 99% homogeneity of the proteins recovered from the process can be obtained.

In a further aspect the invention also includes a process for the production of a precursor of a mature mammalian protein or polypeptide product of sequence X-Pro-Z, the precursor having the sequence Met-Y-X-Pro-Z, wherein Y is a natural amino acid which is specifically cleavable in vitro from Y-X-Pro-Z by an aminopeptidase and imparts resistance to in vivo processing by endogenous bacterial aminopeptidases, X is a single N-terminal amino acid other than proline and Z is the remaining amino acid sequence of the mature product, comprising expressing the precursor in bacterial host cells, provided that Y is not Leu when X-Pro-Z is mature bovine growth hormone.

In a yet further aspect the invention includes a process for the production of a mature mammalian protein or polypeptide product of sequence X-Pro-Z wherein X is a single N-terminal amino acid other than proline and Z is the remaining amino acid sequence of the mature product, comprising treating a precursor which has the sequence Met-Y-X-Pro-Z wherein X and Z are as defined above and Y is a natural amino acid which is specifically cleavable in vitro from Y-X-Pro-Z by an amino-peptidase and imparts resistance to in vivo processing by endogenous bacterial aminopeptidases, with an aminopeptidase to yield the mature product, provided that Y is not Leu when X-Pro-Z is mature bovine growth.

Typically the Met-Y-X-Pro-Z precursor of this latter aspect is produced by expression in bacterial host cells. Preferably also the Met-Y-X-Pro-Z precursor is isolated prior to in vitro treatment with the aminopeptidase to yield the mature product.

In a still further aspect the invention includes an N-terminal extended precursor of a mature mammalian protein or polypeptide product having the sequence Met-Y-X-Pro-Z or Y-X-Pro-Z wherein X-Pro-Z is the sequence of the mature product and wherein X is a single amino acid other than proline, Z is the remaining amino acid sequence of the mature product and Y is a natural amino acid which is specifically cleavable in vitro from Y-X-Pro-Z by an amino-peptidase and imparts resistance in vivo to processing by endogenous bacterial aminopeptidases, provided that Y is not Leu when X-Pro-Z is mature bovine growth hormone.

We have found in the case of IL-6 that the some of the Met-Y-IL-6 and Y-IL-6 precursors have IL-6 like biological activity. In some cases, e.g. Met-Phe-IL-6, this biological activity is equivalent to that of the Ala-Pro-Z mature protein. It is expected that other Met-Y-X-Pro-Z and Y-X-Pro-Z precursors will have biological activity corresponding to that of their mature X-Pro-Z protein counterparts. Such biologically active precursors may be used as pharmaceutical active ingredients in the same indications as their mature X-Pro-Z protein counterparts.

Embodiments of the invention are now described by way of example only.

EXAMPLE 1

Production of LIF a) Preparation of Clones

A polymerase chain reaction (PCR) is performed to generate DNA-sequences which code for Met-Y-LIF; where Y is Phe, His or Ile. The LIF coding sequence is used as the template. The gene for human LIF is reported in Gough, H. et al; 1988; *Proc. natl. Acad. Sci, US*, 85; 2623–2627. The 5' primer is an oligonucleotide which specifies the first 15 amino acids of LIF and the additional amino acid Y. The 5' oligonucleotide also contains a HpaI restriction site at its 5' end. A 3' oligonucleotide which specifies the unique sequence of the 3' end of the LIF gene and which also contains a HpaI restriction site at its 3' end is selected as the PCR partner. The polymerase chain reaction is then run to provide vectors containing the DNA sequences. PCR techniques are conventional and are discussed in Marx, J. L.; 1988; *Science*; 240, 1408–1410 and Saiki, R. K. et al; 1988; *Science*; 239, 487–491.

The PCR products containing the Met-Y-LIF coding regions are excised as HpaI-HpaI fragments and are cloned into the HpaI restriction site of the expression plasmid $pP_L$ obtainable from Pharmacia. Care is exercised to ensure that the correct-sized fragments are cloned into the plasmid, and the plasmids having the fragments in the correct orientation are selected for further use.

In this plasmid the $\lambda P_L$ promoter is controlled by the cI repressor of phage $\lambda$. The promoter may be thermoregulated by using a bacterial host strain, such as N4830-1, which contains the temperature sensitive cI857 repressor. At low temperature (29–31° C.) the cI857 repressor maintains the promoter in the repressed state; whilst raising the temperature, e.g. to 42° C., destroys the repressor activity and allows extensive transcrition from the $P_L$ promoter. In bacterial hosts which carry the cI+ repressor, the $\lambda P_L$ promoter may be induced by the addition of nalidixic acid to the growth medium (Mott et al. PNAS 82, 88, (1985)).

The Met-Y-LIF expression plasmids are transformed into a suitable *E. coli* host strain, such as N4830-1 and transformants selected and maintained on ampicillin (the $pP_L$ plasmid has an ampicillin resistance marker gene). Transformants are grown on nutrient medium and Met-Y-LIF products recovered.

Met-Y-LIF products isolated from the *E. coli* containing the expression plasmids are characterized by Edman analysis. They are essentially homogeneous and contains an N-terminal Met as expected. The *E. coli* expressing the plasmid Met-Ile-LIF is selected for further processing. A single colony derived from this strain is selected for fermentation.

For comparison, a plasmid coding for Met-LIF is also introduced into the *E. coli* host. The characterization, by Edman analysis, of the expression product subsequently purified from the *E. coli* containing the plasmid Met-LIF shows it to be a heterogeneous mixture consisting of 79% of Met-LIF, 12% of correctly processed LIF and 9% LIF with an N-terminal Pro (which is normally the second amino acid residue of LIF).

b) Expression of Met-Ile-LIF

A pre-culture of the selected clone is prepared and is used as an inoculum for fermentation. A fermenter is filled with a sterile salt and trace metal solution and the temperature of the solution is maintained at 30° C. and the pH at 7. The solution is aerated and stirred at 300 rpm.

The fermentation is then initiated by adding the inoculum to the fermenter. A nutrient solution containing 2 g/l yeast extract (BBL) and 7 g/l Casamino acids is then added as necessary. A glucose solution containing 550 g/l glucose.$1H_2O$ and an ammonia solution (conc 25% $NH_4OH$) is added at intervals to return the pH of the solution to 7. The growth phase is continued until an optical density ($OD_{550}$) between 7 and 15 is reached.

Met-Ile-LIF expression from the *E coli* is then induced by shifting the temperature from 30° C. to 42° C. Further nutrient medium is added as necessary. Feeding of the glucose and ammonia solutions is continued.

After three hours of induction, the fermentation is terminated by harvesting the culture broth into mobile vessels which are transferred to a centrifuge. Centrifugation is carried out using a tubular centrifuge (Padberg Z 41) at 18000 g and for a mean residence time of 150 seconds.

c) Isolation of Met-Ile-LIF

Wet *E. coli* pellets obtained from the centrifuge are added to ice-cold buffer A (50 mM Tris-HCl pH 8.0; containing 2 mM DTT (dithiothreitol), 5 mM Benzamidine-HCl and 1 mM EDTA) and the solution is vigorously stirred on ice to bring the cells into suspension. The suspended cells are then lysed by passage through a Manton-Gaulin homogenizer (2 passes at 1200 bar) after which the lysate is diluted 2-fold with buffer A to aid centrifugation.

The diluted cell lysate is centrifuged for 30 min at 16000 g. The pellet is resuspended in buffer A, passed once more through the Manton-Gaulin homogenizer and then centrifuged as before. This wash process is repeated once more, but with reduced centrifugation (25 min at 13000 g). The resultant pellet is then suspended in water, centrifuged as previously described, weighed and frozen at −20° C.

The frozen pellet, which contains LIF inclusion bodies, is resuspended in solubilization buffer (buffer B: 0.1M Glycine-HCl pH 3.0; containing 8.5M Urea) at 50 ml/g. After 30 minutes of stirring at room temperature, DTT (dithiothreitol) is added to 100 mM and the mixture stirred overnight under vacuum.

The reduced, solubilized inclusion bodies are then centrifuged (25 min; 13000 g) and the supernatant decanted and filtered. The filtered supernatant is loaded at a flow-rate of 50 ml/min onto an XK50/20 column of Pharmacia S-Sepharose Fast Flow pre-equilibrated with buffer B. Chromatography is carried out at room temperature. After loading, the column is washed with buffer C (50 mM citric acid/NaOH pH 5.0; containing 8.5M Urea and 100 mM NaCl). During the wash, a sharp yellow band forms at the top of the column and gradually migrates downwards. Once this band has eluted, the buffer C wash is replaced by a 100 to 1000 mM NaCl gradient formed over 800 ml. A single protein peak is eluted, collected manually and the volume measured.

The eluted peak is immediately diluted to 2M Urea by the addition of 3 volumes of degassed 100 mM acetic acid and left under vacuum (60 mmHg) until an accurate HPLC protein determination can be carried out. This "rapid dilution" step to 2M Urea is carried out to initiate refolding. Once the protein determination has been carried out, the Met-Ile-LIF is further diluted with 50 mM acetic acid (containing 2M Urea) until a protein concentration of 50 μg/ml is reached.

Solid Tris is added to the diluted Met-Ile-LIF solution, to 50 mM, followed by oxidized glutathione (GSSG) to a 1.5 molar excess. The solution is adjusted to pH 8.0 by addition of 5N NaOH and stirred at room temperature. After 3 to 5 hours, the pH is re-adjusted upwards to 8.0, and after 20 hours glacial acetic is added to bring the pH to 5.0.

The oxidized, acidified Met-Ile-LIF solution is filtered using a Sartobran 0.45/0.22 μm dual membrane filter. The filtrate is then concentrated by ion-exchange chromatography on S-Sepharose F XK 50/15 (equilibrated and run at 50 ml/min with buffer D; 50 mM NaAcetate pH 5.0). After loading, the column is washed with buffer D until the U.V. trace returns to background. Then a salt gradient is applied (0 to 1M NaCl in buffer D over 800 ml) to elute the Met-Ile-LIF.

The resultant Met-Ile-LIF pool (400 to 600 ml) is concentrated to 1 mg/ml and filtered through a 0.2 μm filter. The filtrate is then loaded as 15 ml injections onto a Pharmacia Hi-Load Superdex XK 26/60 gel filtration column equilibrated with PBS pH 7.2. Monomeric Met-Ile-LIF (eluting at 160 to 225 ml) is then pooled. Met-Ile-LIF monomers are concentrated to 0.5 to 1.0 mg/ml in order to facilitate efficient digestion with AP-1. The concentrated, monomeric Met-Ile-LIF is substantially homogeneous.

d) Aminopeptidase Treatment

Treatment of the concentrated, monomeric Met-Ile-LIF is carried out overnight at room temperature using an enzyme: substrate ratio of 1:600 and a Met-Ile-LIF concentration of 0.5 mg/ml. The enzyme is previously prepared from a stock solution of 0.5 mg/ml by dilution of 26 μg/ml and heat inactivation of any contaminating activities by pre-incubation at 70° C. for 3 hours. After treatment, the reaction is stopped by addition of glacial acetic acid to pH 5.0 and the solution filtered before loading onto an XK26/3 column of Pharmacia DEAE Fast Flow which has been pre-equilibrated with 50 mM Tris/HCl pH 8.0. The LIF (unbound under these conditions) is collected and sterile filtered.

After 1 hour of treatment, 91.4% of the protein has been digested down to LIF having Ser at the N-terminus. After 24 hours of treatment, 100% LIF having Ser at the N-terminus is obtained.

EXAMPLE 2

Production of IL-6 a) Preparation of Clones

A polymerase chain reaction (PCR) is performed to generate DNA sequences which code for Met-Y-IL-6; where Y is Ser, Asn, Gln, His, Arg, Lys, Tyr, Phe, Met, Val, Ile, or Leu in a conventional manner. The polymerase chain reaction is then run to provide vectors containing the DNA sequences. The twelve PCR products containing the Met-Y-IL-6 coding regions are then each cloned into the expression plasmid described in example 1.

The plasmids are then each introduced into the E. coli host by the same technique as used in example 1. The plasmids are maintained by ampicillin selection as before.

b) Expression of Met-Y-IL-6

The E. coli are fermented in a conventional manner and the expression of Met-Y-IL-6 products induced. The fermentation is terminated by harvesting the culture broth into mobile vessels which are transferred to a centrifuge. Centrifugation is then carried out.

c) Isolation of Met-Y-IL-6

Wet E. coli pellets obtained from the centrifuge are then resuspended in buffer. The suspended cells are then lysed by passage through a glassball-mill or a high pressure homogenizer.

The diluted cell lysate is centrifuged and the resultant supernatant (including viscous material) is decanted and the pellet is collected.

The pellets, which contain Met-Y-IL-6 inclusion bodies, are suspended in a solution of 7M guanidine hydrochloride/5 mM DTT/Tris buffer pH 8 to solubilize the protein.

The reduced, solubilized protein is then oxidatively refolded by diluting the solution to 1M guanidine hydrochloride in the presence of an appropriate amount of oxidized glutathione and Tris buffer at pH 8.0. After 5 hours, the solution is further diluted, adjusted to pH 5 and filtered. The protein is then isolated by chromatography on S-Sepharose FF. The composition of the N-terminus of each Met-Y-IL-6 protein is then determined by Edman analysis.

d) Aminopeptidase Treatment

Treatment of the Met-Y-IL-6 protein is carried out for 3 hours at 37° C. and pH 7 using an enzyme:substrate ratio of 1:1000. After treatment, the reaction is stopped by filtering the solution through a Q-Sepharose column. The composition of the N-terminus of each IL-6 protein is then determined by Edman analysis.

The protein yields for a given cell density for each Met-Y-IL-6 protein and the ratio of the detected N-terminal sequences in the products are given in Table 1.

TABLE 1

| Yields of Met-Y-IL-6 protein | | |
|---|---|---|
| | Met-Y-IL-6/Y-IL-6/IL-6 percentage | Yield of |
| Y | Before AP-1 | After AP-1 | Met-Y-IL-6 |
| Ser | <1/100/<1 | <1/84/16 | 11.8 mg |
| Asn | 86/14/<1 | <1/45/55 | 10.8 mg |
| Gln | 100/<1/<1 | <1/71/27 | 6.9 mg |
| His | 100/<1/<1 | <1/5/95 | 12.6 mg |

TABLE 1-continued

Yields of Met-Y-IL-6 protein

| Y | Met-Y-IL-6/Y-IL-6/IL-6 percentage | | Yield of Met-Y-IL-6 |
|---|---|---|---|
| | Before AP-1 | After AP-1 | |
| Arg | 100/<1/<1 | <1/56/44 | 15.0 mg |
| Lys | 100/<1/<1 | <1/60/40 | 20.0 mg |
| Tyr | 100/<1/<1 | <1/38/62 | 10.4 mg |
| Phe | 100/<1/<1 | <1/<1/100 | 11.0 mg |
| Met | 100/<1/<1 | <1/<1/100 | 6.9 mg |
| Val | 2/93/<1[1] | <1/<1/96[2] | 5.6 mg |
| Ile | 79/21/<1 | <1/<1/100 | 3.7 mg |
| Leu | 97/3/<1 | <1/<1/100 | 3.8 mg |

[1] 5% Pro$^2$-Val$^3$-Pro$^4$-Z was also obtained.
[2] 4% Val$^3$-Pro$^4$-Z was also obtained, which is explained by AP-1 cleavage of Pro$^2$-Val$^3$-Pro$^4$-Z.

In comparison, repeating the process for the corresponding plasmid that contains DNA coding for Met-IL-6 gives the following results:

Protein Yield: 20.0 mg

Met-Ala-Pro-Z (SEQ. ID NO. 7): 33%

Ala-Pro-Z: 16% (3.2 mg)

Pro-Z: 51%

Therefore for IL-6, substantially homogeneous protein is obtained when Y is His, Phe, Met, Ile and Leu and of these yield is highest when Y is His, Met and Phe.

What is claimed is:

1. A process for the recombinant production in a bacterial host of the mature form of a mammalian protein which is subject to processing by endogenous bacterial aminopeptidases of the formula X-Pro-Z, comprising the steps of:
   a) transforming bacterial host cells with an appropriate vector containing DNA coding for Met-Y-X-Pro-Z (SEQ. ID NO. 1);
   b) inducing the cell to express the Met-Y-X-Pro-Z product;
   c) treating the Met-Y-X-Pro-Z product with an appropriate aminopeptidase to cleave off Met and Y; and
   d) isolating the resulting protein X-Pro-Z, wherein X-Pro-Z is human interleukin 6 (IL-6) or leukemia inhibitory factor (LIF), X is a single N-terminal amino acid other than proline, Z is the remaining sequence of amino acid residues of the protein, and Y is a natural amino acid selected from Ser, Asn, Gln, His, Arg, Lys, Tyr, Phe, Met, Val, Ile and Leu which is specifically cleavable in vitro from Y-X-Pro-Z (SEQ. ID NO. 2) by an aminopeptidase and imparts resistance to in vivo processing by endogenous bacterial aminopeptidases.

2. A process for the production of a precursor of a mature mammalian protein product of sequence X-Pro-Z, which comprises expressing the precursor in bacterial host cells, the precursor having the sequence Met-Y-X-Pro-Z (SEQ. ID NO. 1), wherein X-Pro-Z is IL-6 or LIF, Y is a natural amino acid selected from Ser, Asn, Gln, His, Arg, Lys, Tyr, Phe, Met, Val, Ile and Leu which is specifically cleavable in vitro from Y-X-Pro-Z (SEQ. ID NO. 2) by an aminopeptidase and impart resistance to in vivo processing by endogenous bacterial aminopeptidases, X is a single N-terminal amino acid other than proline, and Z is the remaining amino acid sequence of the mature product.

3. A process for the production of a mature mammalian protein product of sequence X-Pro-Z, which comprises treating a precursor which has the sequence Met-Y-X-Pro-Z (SEQ. ID NO. 1) with an aminopeptidase to yield the mature product, wherein X-Pro-Z is IL6 or LIF, X is a single N-terminal amino acid other than proline, Z is the remaining amino acid sequence of the mature product, and Y is a natural amino acid selected from Ser, Asn, Gln, His, Arg, Lys, Tyr, Phe, Met, Val, Ile and Leu which is specifically cleavable in vitro from Y-X-Pro-Z (SEQ. ID NO. 2) by an aminopeptidase and imparts resistance to in vivo processing by endogenous bacterial aminopeptidases.

4. A process according to claim 1, in which the protein X-Pro-Z is IL-6 and Y is Phe, His, Met, Ile or Leu.

5. A process according to claim 4 in which Y is Phe, His or Met.

6. A process according to claim 1 in which the protein X-Pro-Z is LIF and Y is His, Phe or Ile.

7. A process according to claim 6 in which Y is Ile.

8. A process according to claim 1 in which the bacterial host is *E. coli*.

9. A process according to claim 1 in which the aminopeptidase used to cleave off Met and Y is selected from those obtained from *Bacillus stearothermophilus, Streptomyces griseus* or Aeromonas.

10. A process according to claim 9 in which the aminopeptidase is obtained from Aeromonas.

11. An N-terminal extended precursor of a mature mammalian protein product having the sequence Met-Y-X-Pro-Z (SEQ. ID NO. 1) or Y-X-Pro-Z (SEQ. ID NO. 2), wherein X-Pro-Z is IL-6 or LIF, X is a single amino acid other than proline, Z is the remaining amino acid sequence of the mature product, and Y is a natural amino acid selected from Ser, Asn, Gln, His, Arg, Lys, Tyr, Phe, Met, Val, Ile and Leu which is specifically cleavable in vitro from Y-X- Pro-Z (SEQ. ID NO. 2) by an aninopeptidase and imparts resistance to in vivo processing by endogenous bacterial aminopeptidases.

12. A precursor according to claim 11 in which X-Pro-Z is IL-6 and Y is Phe, His, Met, Ile or Leu.

13. A precursor according to claim 11 in which X-Pro-Z is LIF and Y is His, Phe or Ile.

* * * * *